(12) United States Patent
Yoshida et al.

(10) Patent No.: US 9,642,684 B2
(45) Date of Patent: May 9, 2017

(54) ELECTRIC TOOTHBRUSH

(71) Applicant: SUNSTAR INC., Takatsuki-shi (JP)

(72) Inventors: Kazuaki Yoshida, Takatsuki (JP); Masahiro Nishiura, Takatsuki (JP)

(73) Assignee: SUNSTAR INC., Takatsuki-shi (JP)

( * ) Notice: Subject to any disclaimer, the term of this patent is extended or adjusted under 35 U.S.C. 154(b) by 0 days.

(21) Appl. No.: 14/774,441

(22) PCT Filed: Mar. 7, 2014

(86) PCT No.: PCT/JP2014/055977
§ 371 (c)(1),
(2) Date: Sep. 10, 2015

(87) PCT Pub. No.: WO2014/142029
PCT Pub. Date: Sep. 18, 2014

(65) Prior Publication Data
US 2016/0022393 A1    Jan. 28, 2016

(30) Foreign Application Priority Data
Mar. 11, 2013    (JP) .................................. 2013-048109

(51) Int. Cl.
*A46B 15/00* (2006.01)
*A61C 17/22* (2006.01)
*A61C 17/34* (2006.01)

(52) U.S. Cl.
CPC ...... *A61C 17/3481* (2013.01); *A46B 15/0006* (2013.01); *A61C 17/221* (2013.01); *A61C 17/225* (2013.01); *A46B 2200/1066* (2013.01)

(58) Field of Classification Search
CPC .............. A46B 15/0006; A61C 17/221; A61C 17/3481
See application file for complete search history.

(56) References Cited

U.S. PATENT DOCUMENTS

| | | | |
|---|---|---|---|
| 9,144,476 B2 * | 9/2015 | Iwahori | A46B 15/0006 |
| 2003/0135940 A1 | 7/2003 | Lev | |
| 2010/0106336 A1 * | 4/2010 | Hwang | A46B 15/0006 700/280 |

FOREIGN PATENT DOCUMENTS

| | | |
|---|---|---|
| JP | 2008-543418 A1 | 12/2008 |
| JP | 2009-219757 A1 | 10/2009 |
| JP | 2009-240759 A1 | 10/2009 |
| JP | 2010-213908 A1 | 9/2010 |
| JP | 2011-136146 A1 | 7/2011 |

OTHER PUBLICATIONS

International Search Report for International Application No. PCT/JP2014/055977 dated May 27, 2014.

* cited by examiner

*Primary Examiner* — Randall Chin
(74) *Attorney, Agent, or Firm* — Kratz, Quintos & Hanson, LLP

(57) ABSTRACT

An electric toothbrush with a thinner handle part to ensure the ease of manual tooth-brushing while improving the ease of a switch operation between the operating state and the stopped state, the electric toothbrush being configured to realize an effective oral cleaning by automatically giving a necessary mechanical assistance to a brush part according to the brushing state constantly varying during tooth-brushing depending on the cleaned part and the ways of holding and moving the toothbrush.

8 Claims, 11 Drawing Sheets

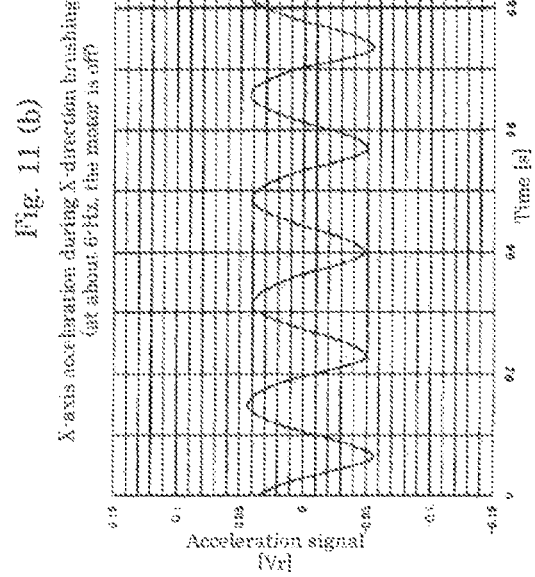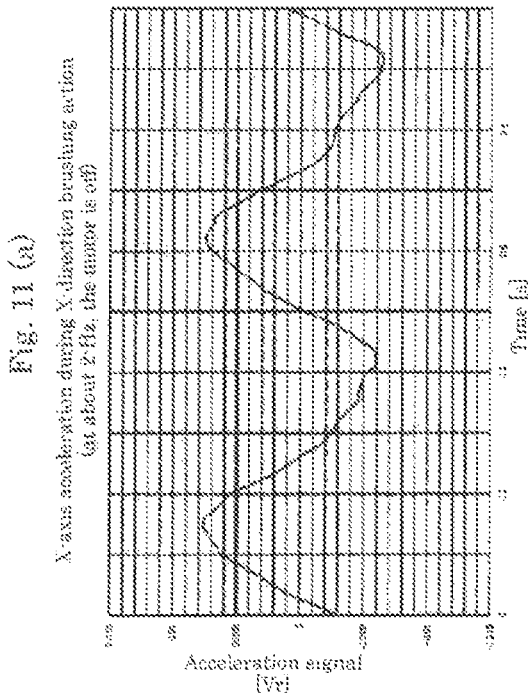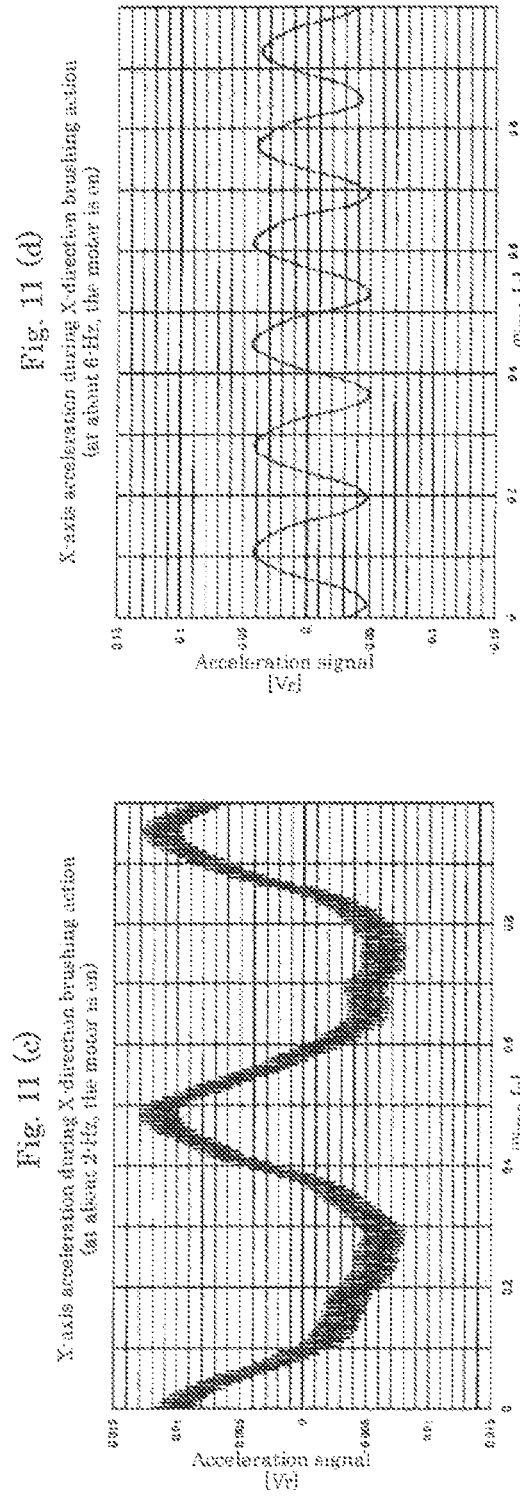

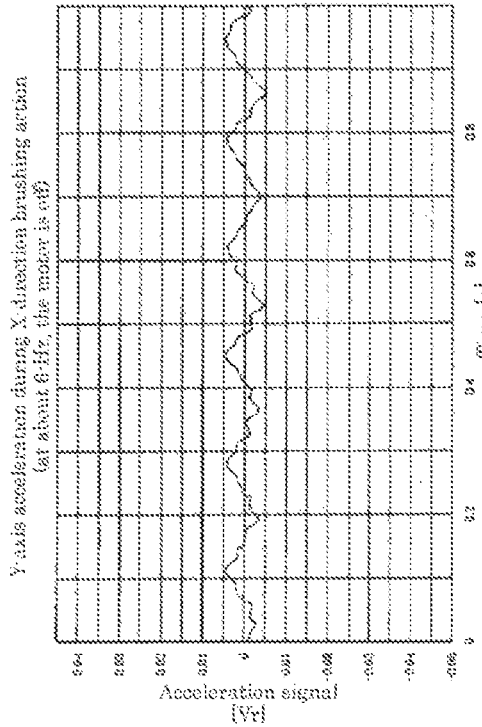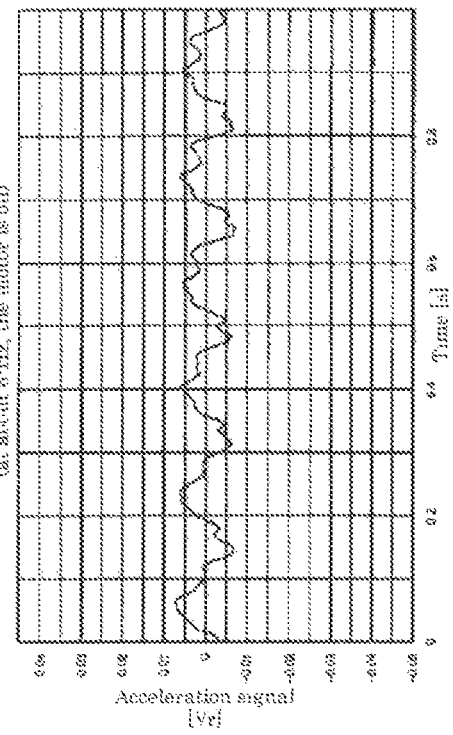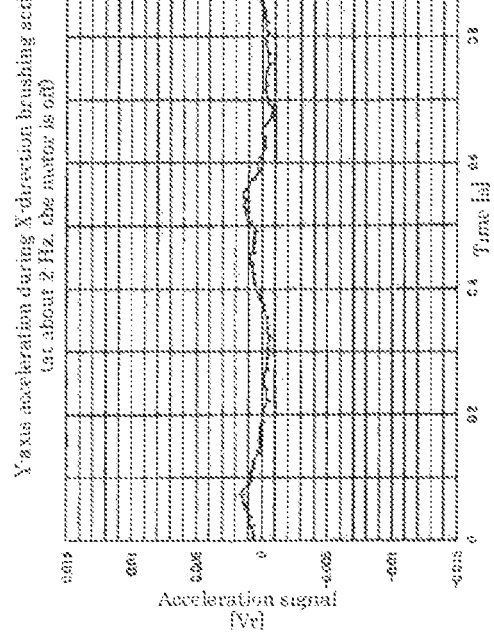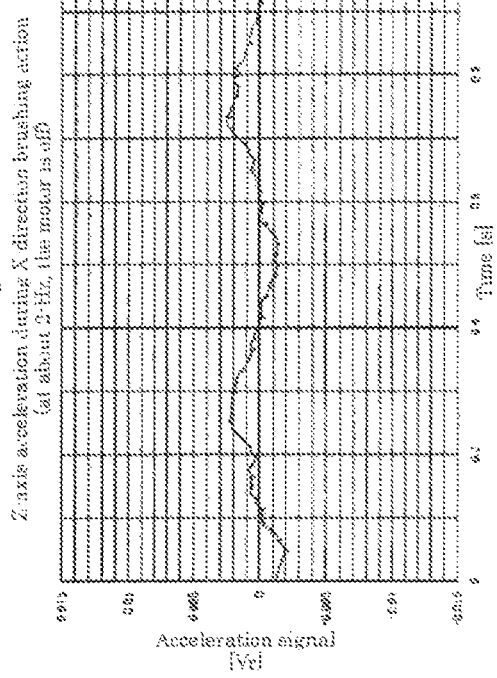

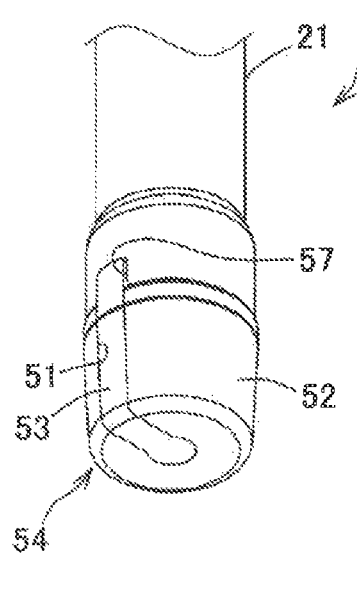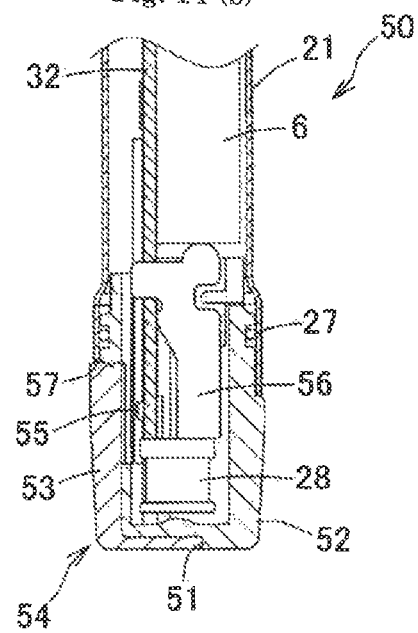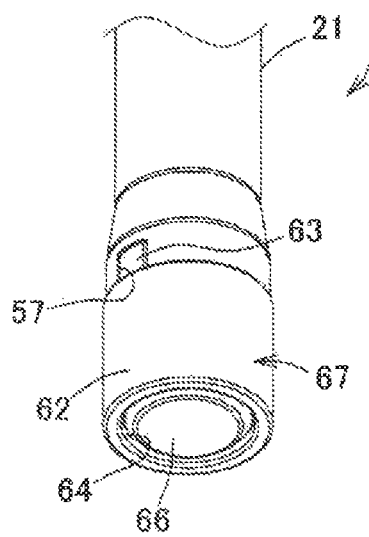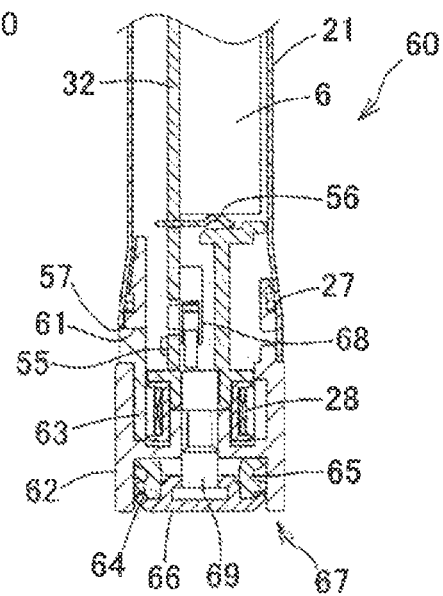

ELECTRIC TOOTHBRUSH

TECHNICAL FIELD

The present invention relates to an electric toothbrush with which the cleaning power of a manual brushing action can be assisted by the cleaning power obtained by electromotion.

BACKGROUND ART

There are widely used electric toothbrushes of several types including: a linear motion type having a conversion means for converting the rotational motion of a motor into the reciprocating linear motion of a brush part; an inverse motion type having a conversion means for converting the rotational motion of a motor into the reciprocating inverse motion of a brush part; a weight vibration type that rotates a weight by a motor to vibrate a brush part; and a linear vibration type that causes a brush part to reciprocate and vibrate by a linear actuator.

There are widely used power switches for electric toothbrush including a mechanical power switch with a push button-type or slide-type electric contact (for example, refer to Patent Document 1).

There has been proposed an electric toothbrush including an acceleration sensor such that the brushing position is estimated according to a signal from the acceleration sensor and the vibration mode is switched (for example, refer to Patent Document 2).

CITATION LIST

Patent Literatures

Patent Document 1: JP-A No. 2011-136146
Patent Document 2: JP-A No. 2009-240759

SUMMARY OF INVENTION

Technical Problem

The linear motion-type, inverse motion-type, or linear vibration-type electric toothbrush provides a strong brushing power by an electric motor, but is complicated in structure and has a thick handle part or a heavy brush part. In particular, with a plurality of vibration modes, the electric toothbrush also comes to have a complicated switch part. In addition, since the switch is to be operated while holding the toothbrush, the switch needs to be positioned on the periphery of the handle part, and thus the handle may be further thicker and the toothbrush further heavier. The toothbrush with a thick handle part or the entirely heavy toothbrush is hard to hold firmly and continuously for children and women with small hands, and children, elderly persons, and sick persons with a weak grip or a low physical endurance. Accordingly, such persons cannot take a sufficient time for brushing the teeth and may be in unfavorable oral cleaning state in spite of brushing the teeth.

Meanwhile, in the case of using a manual toothbrush, the cleaning performance of the toothbrush is significantly influenced by physical force during motion of filament bristles back and forth on the surface of a tooth surface or the like. Accordingly, to clean the teeth effectively, it is preferred to move the bristles back and forth on each of the teeth, and it is thus necessary to learn an appropriate brushing technique for achieving the effective clean state. However, many persons actually brush their teeth in their own ways according to their preferences. Brushing continuously the teeth by excessive power for a long time may cause the problem of scraping off the teeth and gums. To give a sufficiently oral cleaning with no appropriate brushing technique, long-time brushing is required. In this case, however, children, elderly persons, sick persons, and pregnant women may not give their teeth a sufficient cleaning because they may not be able to open their mouths for a long time for tooth-brushing. Further, children, elderly persons, and sick persons having difficulty in self-dental care require a further higher toothbrushing technique for oral care by themselves or helpers. However, only a few of these persons have such a technique, and thus children, elderly persons, and sick persons having difficulty in self-dental care are likely to give an insufficient oral cleaning. It is known that an insufficient oral cleaning may cause not only dental illnesses such as dental caries and periodontal disease but also systemic illnesses such as aspiration pneumonia and early miscarriage. Accordingly, it is a major issue to give a sufficient oral cleaning in a short time for persons in need of care, elderly persons, and pregnant women in particular.

It is conventionally difficult to provide an electric toothbrush with a sufficiently thin brush main body including a handle part because, for moving widely a brush part (with filaments implanted) for vertical motion or rotational motion, it is necessary to provide a mechanical part to transfer the motor's rotational power physically directly to the brush part or supply motion energy for driving the brush part, and thus there is limitation on the size reduction of the motor. Meanwhile, the weight vibration-type electric toothbrushes are configured to vibrate the entire toothbrush by rotating a weight-type movement using power of a rotary motor or reciprocating a weight with a linear motor, and have recently been gaining popularity among young women because these toothbrushes are simple in structure, have a slim and smart handle part, and are capable of being put into their handbags or pochettes. However, the weight vibration-type electric toothbrush obtains a mechanical cleaning power by transferring centroid fluctuations resulting from rotation of a weight-type movement, and thus cannot obtain a sufficient cleaning power because the motion energy given to the brush part is significantly smaller than that in a general electric toothbrush in which the toothbrush head part is moved by physical binding to the motor driving part.

In view of such circumstances, the inventor of the present invention has earnestly studied on development of a power-assisted toothbrush that assists manual brushing, based on the idea that the weight vibration-type electric toothbrush or the like with a thin and slim handle part producing weak brushing power could be improved to produce sufficient brushing power as a whole by making the handle part thinner to be close to the thickness of the handle part of a manual toothbrush to produce sufficient ease of a manual brushing action, and by providing an electrical assistance in the case where sufficient cleaning power cannot be given only by a manual brushing action.

As the result of the study, the inventor has found several problems that, when the handle part of the electric toothbrush is made thin, the push button-type or slide-type power switch needs to be small in size, and thus the power switch is very hard to operate for elderly persons and women with long artificial nails who cannot perform fine finger manipulations, and that, for obtaining a necessary optimum assistance, the power switch needs to be frequently operated according to the state of a tooth-brushing action, but it is difficult to operate the power switch while moving the hand for tooth-brushing. The power switch is preferably operated while the brush part is put in the mouth because if the power switch is operated while toothpaste is put on the brush part before the brush part is put into the mouth, water or toothpaste may drop or scatter from the brush part. However, the inventor has found a problem that, when changing the holding way of the electric toothbrush for tooth-brushing, it is difficult for the user to operate the power switch because he/she needs to search for the power switch only by fingers with significant difficulty in finding the position of the power switch. In addition, the tooth-brushing power varies depending on differences in physical condition, teeth being cleaned, and others. Accordingly, an insufficient cleaning or a cleaning with application of excessive physical force may give a load on the teeth surfaces and cause damage to the same. There is no problem if the user of the toothbrush can control a brushing action while finely sensing the part being cleaned in the mouth by the hand holding the toothbrush. However, when the user of the toothbrush is a sick person, a handicapped person, or a child, he/she may not have such a fine feeling or control the fine hand movement, and thus may not be able to judge the proper degree of necessary assistance or the necessity of assistance, or give a proper brushing. In particular, the toothbrush is harder to operate for persons such as caregivers in charge of brushing the teeth of another person in need of care. Further, for a helper in charge of brushing the teeth of another person in need of care or an infant, he/she needs to hold the toothbrush in a way different from that in brushing of his/her own teeth, and thus the power switch is harder to operate for the helper.

An object of the present invention is to provide an electric toothbrush with a thinner handle part to ensure the ease of manual tooth-brushing while improving the ease of a switch operation between the operating state and the stopped state. More specifically, an object of the present invention is to provide an electric toothbrush that realize an effective oral cleaning by automatically giving a necessary mechanical assistance to a brush part according to the brushing state constantly varying during tooth-brushing depending on the cleaned part and the ways of holding and moving the toothbrush.

Solution to Problem

An electric toothbrush according to the present invention includes: a toothbrush main body having a toothbrush head part and a handle part for manually operating the toothbrush head part; a vibration generation means that vibrates the toothbrush head part; an acceleration sensor that detects a manual brushing action; and a control means that controls at least the vibration generation means to switch between the operating state and the stopped state, according to output from the acceleration sensor. In addition, the acceleration of the electric toothbrush during a brushing action or a handling operation, for example, falls within a predictable range in usual indoor use situations. Accordingly, the driving of the electric toothbrush can be controlled by detection of the acceleration. However, in other situations, for example, while the electric toothbrush shipped from the production plant is being distributed or the user is carrying the electric toothbrush, the electric toothbrush undergoes acceleration forces of various magnitudes and some of the acceleration forces may be equivalent to those in the usual indoor use situations. Accordingly, the electric toothbrush may malfunction under the control conditions based on the usual indoor use situations. Therefore, the electric toothbrush is preferably provided with a malfunction prevention mechanism to prevent such malfunction.

According to the electric toothbrush, when the toothbrush main body is manually moved for a brushing action, the acceleration sensor detects the acceleration during the brushing action, the control means switches the vibration generation means to the operating state and the vibration generation means gives vibrations to the brush part, whereby the user can brush the teeth and gums by a manual brushing action assisted with electric-powered vibrations. Meanwhile, when the user stops the manual brushing action of the toothbrush main body, the control means switches the vibration generation means to the stopped state according to output from the acceleration sensor. In addition, based on the information on acceleration or the like detected during the brushing action, the electric-powered assistance may be stopped when sufficient brushing is performed, or the degree of the electric-powered assistance may be controlled when insufficient brushing is performed, according to the degree of insufficiency.

As described above, the electric toothbrush is configured based on the assumption that a manual brushing action is performed, and thus the vibration generation means can be of a small size with relatively weak power. Accordingly, it is possible to realize the electric toothbrush suited to a manual brushing action with the slim handle part and the small-sized vibration generation means with relatively weak power, thereby to enhance the ease of the manual brushing action and provide significant brushing performance. In addition, the vibration generation means can be operated by performing a manual brushing action with the toothbrush main body, and the vibration generation means can be stopped by discontinuing the manual brushing action with the toothbrush main body, and the degree of assistance can be automatically determined or changed according to the state of the brushing action. Accordingly, even when elderly persons with a weak feeling of fingers, sick persons and handicapped persons, and women with long and artificial nails brush their teeth or when caregivers brush the teeth of persons in need of care or infants instead of them, they can easily switch the vibration generation means between the operating state and the stopped state and can switch to an appropriate assisted state. The electric toothbrush does not need a mechanical power switch and thus the handle part of the electric toothbrush can be made further thinner and slimmer with reduced asperities on the surface to improve the cleaning performance of the handle part. In addition, the electric toothbrush can be formed of a simplified water-tight structure to improve water tightness and reduce the costs for producing the electric toothbrush. Further, the vibration generation means can be operated by performing a manual brushing action in the state where toothpaste is put on the brush part and the brush part is inserted into the mouth. This prevents the toothpaste from falling or dispersing. Even if the battery becomes out of charge, the electric toothbrush can be used for tooth-brushing as a manual toothbrush. The electric toothbrush in the present invention includes the acceleration sensor, a computation part, a field-effect transistor, a secondary battery, an induction coil and a charging circuit for charging the secondary battery, and is configured such that, when the electric toothbrush is put on an external battery charger, an inductive current is generated in the induction coil to charge the secondary battery. In this configuration, the acceleration sensor and the computation part are both energized during battery charging. Alternatively, during battery charging, the computation part may be in the sleep state and the acceleration sensor in the standby state to minimize power consumption. In the electric toothbrush of the present invention, the secondary battery is used as a power source. By setting the final discharge voltage at the computation part, it is possible to prevent performance degradation due to over discharge of the secondary battery. In this example, when the actual discharge voltage falls below the final discharge voltage, power supply from the secondary battery is discontinued and thus power distribution to the acceleration sensor, the computation part, the field-effect transistor, and others is shut off and the control on the electric toothbrush is completely stopped. To recover the functions of the electric toothbrush from this state, with putting the electric toothbrush on the battery charger as a trigger, an inductive current is generated in the induction coil included in the electric toothbrush, and a voltage prescribed by the field-effect transistor and a regulator is applied to the computation part and others. Alternatively, the electric toothbrush may be provided with a power generation means for generating power by a brushing action such that, using power generation by the power generation means as a trigger, the control means starts a control. In this case, power distribution to the control means and the acceleration sensor can be shut off until a brushing action is started, which is preferred for reducing standby electricity. In addition, the electric toothbrush is preferably provided with a degassing hole mechanism for discharging a generated gas because, when a gas is generated due to deterioration of the secondary battery in the sealed space, the toothbrush main body may bulge, deform, or rupture. In the case of providing the degassing hole mechanism, it is further preferred to provide the electric toothbrush with a breathable film not letting a liquid pass but letting a gas pass, to prevent foreign matter from the outside such as water from flowing into the electric toothbrush.

In a preferred embodiment, the vibration generation means includes a motor and a weight eccentrically rotated by the motor, or includes a linear actuator and a weight reciprocated by the linear actuator. The present invention is applicable to linear motion-type and inverse motion-type electric toothbrushes. In particular, the present invention is preferably suited to weight vibration-type electric toothbrushes including a motor and a weight eccentrically rotated by the motor, and, out of linear vibration-type electric toothbrushes, weight linear vibration-type electric toothbrushes that include a linear actuator and a weight reciprocated by the linear actuator and transfer vibrations to not the casing but the brush part, excluding electric toothbrushes vibrating directly the brush part. That is, in a weight vibration-type or weight linear vibration-type electric toothbrush, vibrations are also transferred to the toothbrush main body and thus the vibrations of the brush part tend to be weak. However, by using a small-sized motor or linear-actuator in the electric toothbrush, it is possible to preferably realize the electric toothbrush with the thin and slim handle part suited to a manual brushing action. Specifically, in the weight vibration-type or weight linear vibration-type electric toothbrush, the outer diameter of the handle part can be set to 8 to 18 mm, preferably 8 to 15 mm, more preferably 8 to 12 mm. According to this configuration, it is possible to provide sufficient operability of the electric toothbrush in performing a manual brushing action while holding the handle part by hand. In addition, to enhance the detection accuracy for a manual brushing action, the control means is preferably provided with a filter circuit to remove a vibration component resulting from the motor or the linear actuator.

The acceleration sensor may detect the motion of the toothbrush main body in an X-axis direction along the length of the toothbrush main body. Specifically, when the user uses the electric toothbrush to perform a manual brushing action by Bass method or scrub method as general tooth-brushing methods, the motion in the X-axis direction along the length of the toothbrush main body is essential. Thus by providing only one acceleration sensor to detect the acceleration in the X-axis direction, it is possible to detect reliably by the acceleration sensor the presence or absence of a brushing action. When an advanced control is required, it is preferred to provide acceleration sensors in two axes included in the surface of the toothbrush head with a bristle-implanted surface, that is, in two directions of the length (X axis) of the handle part and a Y axis orthogonal to the X axis. It is further preferred to provide acceleration sensors in three directions of the X axis, the Y axis, and a Z axis orthogonal to the former two axes (vertical to the bristle-implanted surface of the toothbrush head), thereby to realize a finer control. In this example, the acceleration sensors may be separately provided, but the use of a biaxial acceleration sensor or a triaxial acceleration sensor will preferably produce a space-saving effect and also may reduce manufacturing costs. To detect the presence or absence of a manual brushing action, in the case where the user of the electric toothbrush is a healthy person and is brushing his/her own teeth, when the acceleration sensor detects vibrations of 3 to 7 Hz in the X-axis direction, if a more strict control is needed, vibrations of 3 to 5 Hz in the X-axis direction, it is determined that the user is performing a brushing action. In the case where the user is performing a brushing action on another person's teeth, when the acceleration sensor detects vibrations of 1 to 5 Hz in the X-axis direction, if a more strict control is needed, vibrations of 1 to 3 Hz in the X-axis direction, it is determined that the user is performing a brushing action. Making such determinations prevents malfunction of the electric toothbrush at a non-brushing time. As described above, it is possible to not only change the operations according to the use pattern but also set optimum determination criteria for automatically switching to the assisted mode according to the feature of the product (for example, the toothbrush for caregiving, the toothbrush for children, or the toothbrush for elderly persons). By making these settings, it is possible to not only prevent malfunction of the electric toothbrush at a non-brushing time but also provide the electric toothbrush with an advanced brushing assisting function.

Depending on distribution and storage conditions after the shipment, the electric toothbrush may undergo various unpredictable vibrations and cause a malfunction. Thus, the electric toothbrush may be provided with a mechanism for preventing malfunction during the period of time from the purchase to the actual use after the shipment. The malfunction prevention mechanism may be configured such that, when being deactivated once, the malfunction prevention function cannot be activated again or such that allows the user to freely activate the malfunction prevention function at his/her discretion. In the latter case, the electric toothbrush is provided with a main power switch as a malfunction prevention mechanism to set the on/off state of the malfunction prevention function. The main power switch does not need to be operated during the use of the electric toothbrush, and thus can be provided even at a position where the user cannot operate the power switch while holding the electric toothbrush, unlike the conventional power switch. That is, to realize the thinner electric toothbrush as an advantage of the present invention, it is necessary to provide the mechanism at the end part of the toothbrush main body along the longer side. For example, by providing the main power switch on the surface of the toothbrush main body opposed to the brush part or providing the mechanism for sensing the attachment of a replacement brush to the handle part such that no power is distributed to the acceleration sensor and others when no replacement brush is attached to the handle part, it is possible to prevent malfunction of the electric toothbrush and reduction in operating time of the electric toothbrush due to shutoff of standby electricity. Further, in a preferred embodiment, the electric toothbrush is provided with a threshold storage means for storing in advance a threshold larger than the upper limit for the output from the acceleration sensor during a manual brushing action such that, when the output from the acceleration sensor is equal to or larger than the threshold stored in the threshold storage means, the control means switches the vibration generation means to the stopped state. According to this configuration, when the vibration generation means is not stopped even though a brushing action is discontinued, the user can shake strongly the electric toothbrush to stop the vibration generation means in a forcible manner. In addition, when the hard-material part of the toothbrush collides against the teeth, the acceleration sensor can detect the impact of the collision and switch temporarily the vibration generation means to the stopped state. Specifically, in the case of helping a child, an elderly person, or a physically handicapped person in tooth brushing, the hard-material part of the toothbrush main body operated by the helper may collide against the teeth of the person in need of help to cause discomfort to the person in need of help. In such a case, the electric toothbrush may be configured such that the vibration generation means can be stopped for a moment to inform the helper of the accident.

The control means preferably controls the number of vibrations from the vibration generation means according to the output from the acceleration sensor. For example, to perform tooth brushing by a uniform brushing power, the number of vibrations from the vibration generation means may be set to be larger when the acceleration resulting from a manual brushing action is low, and the number of vibrations from the vibration generation means may be set to be smaller when the acceleration resulting from a manual brushing action is high. In contrast, to control the number of vibrations from the vibration generation means in cooperation with manual brushing power, the number of vibrations from the vibration generation means may be set to be lower when the acceleration resulting from a manual brushing action is small, and the number of vibrations from the vibration generation means may be set to be larger when the acceleration resulting from a manual brushing action is high. Further, the brush part may be vibrated in vibration forms according to the brushing method with assistance such as Bass method, scrub method, rolling method, or Fones method determined based on the output from the acceleration sensor.

By providing an output means for outputting information to the user and using the acceleration sensor in combination with any other sensors such as a geomagnetic sensor, a gyro sensor, a load sensor, a pressure sensor, a temperature sensor, and an optical sensor in the control means, for example, it is possible to add various functions to the electric toothbrush according to the present invention based on the outputs from these sensors. For example, by analyzing the direction of inclination of the toothbrush relative to the brushed portion and the brushing action, it is possible to determine whether the user is performing a proper brushing action, provide the user with instructive information through the output means so that the user can perform a proper brushing action, and add an educational program function to allow the user to brush his/her teeth within a proper brushing pressure range. By providing the toothbrush head part with an optical sensor, it is possible to detect the start time and the end time of tooth-brushing, prevent malfunction of the electric toothbrush at a higher accuracy in combination with information from the acceleration sensor, and comprehend the detailed state of a brushing action. In this configuration, the user can perform a brushing action with the toothbrush main body according to the instructive information from the output means to learn the correct brushing method. For example, the proper value for the number of reciprocations of the toothbrush per minute in a manual brushing action (hereinafter, referred to also as brushing frequency) may be stored in advance so that the brushing frequency is calculated from the waveform output from the acceleration sensor during tooth-brushing, it is determined whether the number of vibrations falls within the preset proper value, and when the number of vibrations is smaller than the proper value, the user is instructed to increase the brushing speed, and when the number of vibrations is larger than the proper value, the user is instructed to decrease the brushing speed. The electric toothbrush may be provided with a posture detection part for detecting the posture of the electric toothbrush, such as a geomagnetic sensor, a gyro sensor, or a triaxial acceleration sensor, such that the control means stores in advance the output from the posture detection part indicating the postures of proper manual brushing by each of the Bass method, the scrub method, the rolling method, and the Fones method, the output from the posture detection part during the user's actual tooth-brushing is analyzed, and the user is guided to a brushing action by a correct method through audio output or the like, and the number and direction of vibrations and amplitude of the vibration generation means are controlled to determine the degree of assistance and/or the method of assistance.

In another preferred embodiment, the electric toothbrush is provided with an output means for outputting information to the user, and the control means determines whether the vibration generation means normally operates according to the output from the acceleration sensor, and when determining the operation of the vibration generation means as abnormal, provides the user with the information on current operation through the output means. According to this configuration, it is possible to inform the user that the electric toothbrush is out of battery or is defective. Specifically, the proper value for the number of vibrations of the brush part caused by the vibration generation means is measured and stored in advance, the number of vibrations in the waveform output from the acceleration sensor during operation of the vibration generation means is measured, it is determined whether the number of measured vibrations falls within the preset proper value, and when the number of measured vibrations is smaller or larger than the proper value, the user is informed that the vibration generation means does not operate normally.

It is also preferred that the electric toothbrush is provided with one or two or more selected from a temperature sensor that detects whether the user holds the handle part by hand, an optical sensor that detects a replacement brush is attached to or detached from the toothbrush main body, and a pressure sensor that detects pressure acting on the brush part, and the control means controls the vibration generation means according to the outputs from these sensors and the output from the acceleration sensor. The acceleration sensor alone can detect the presence or absence of a manual brushing action. However, the use of the temperature sensor, the optical sensor, and the pressure sensor in combination with the acceleration sensor will realize higher-accuracy detection of the presence or absence of a manual brushing action.

Advantageous Effects of Invention

According to the present invention, the electric toothbrush is configured based on the assumption that a manual brushing action is performed, and thus the vibration generation means can be of a small size with relatively weak power. Accordingly, it is possible to realize the electric toothbrush suited to a manual brushing action with the slim handle part and the small-sized vibration generation means with relatively weak power, thereby to enhance the ease of the manual brushing action and provide significant brushing performance. In addition, the vibration generation means can be operated by performing a manual brushing action with the toothbrush main body, and the vibration generation means can be stopped by discontinuing the manual brushing action with the toothbrush main body, and the degree of assistance can be automatically determined or changed according to the state of the brushing action. Accordingly, even when elderly persons with a weak feeling of fingers, sick persons and handicapped persons, and women with long and artificial nails brush their teeth or when caregivers brush the teeth of persons in need of care or infants instead of them, they can easily switch the vibration generation means between the operating state and the stopped state. Further, the degree of assistance in brushing can be automatically changed according to the state of a brushing action to control a more effective and correct brushing state. The electric toothbrush does not need a mechanical power switch and thus the handle part of the electric toothbrush can be made further thinner and slimmer with reduced asperities on the surface to improve the cleaning performance of the handle part. In addition, the electric toothbrush can be formed of a simplified water-tight structure to improve water tightness and reduce the costs for producing the electric toothbrush. Furthermore, the vibration generation means can be operated by performing a manual brushing action in the state where toothpaste is put on the brush part and the brush part is inserted into the mouth. This prevents the toothpaste from falling or dispersing. Even if the battery becomes out of charge, the electric toothbrush can be used for toothbrushing as a manual toothbrush.

BRIEF DESCRIPTION OF THE DRAWINGS

FIG. 11($a$) is a graph of output from an X-axis acceleration sensor when brushing is performed at a frequency of 2 Hz during stoppage of the motor, FIG. 11($b$) is a graph of output from the X-axis acceleration sensor when brushing is performed at a frequency of 6 Hz during stoppage of the motor, FIG. 11($c$) is a graph of output from the X-axis acceleration sensor when brushing is performed at a frequency of 2 Hz during operation of the motor, and FIG. 11($d$) is a graph of output from the X-axis acceleration sensor when brushing is performed at a frequency of 6 Hz during operation of the motor;

FIG. 12($a$) is a graph of output from a Y-axis acceleration sensor when brushing is performed at a frequency of 2 Hz during stoppage of the motor, FIG. 12($b$) is a graph of output from the Y-axis acceleration sensor when brushing is performed at a frequency of 6 Hz during stoppage of the motor, FIG. 12($c$) is a graph of output from a Z-axis acceleration sensor when brushing is performed at a frequency of 2 Hz during stoppage of the motor, and FIG. 12($d$) is a graph of output from the Z-axis acceleration sensor when brushing is performed at a frequency of 6 Hz during stoppage of the motor;

FIG. 14($a$) is a perspective view of a lower structure of another electric toothbrush and FIG. 14($b$) is a vertical cross-sectional view of the same;

FIG. 15($a$) is a perspective view of a lower structure of another electric toothbrush and FIG. 15($b$) is a vertical cross-sectional view of the same;

DESCRIPTION OF EMBODIMENTS

Embodiment for carrying out the present invention will be described below with reference to the accompanying drawings. In this embodiment, the upper and lower sides are defined relative to an electric toothbrush vertically positioned with a replacement brush at the upper side.

Figure 1:
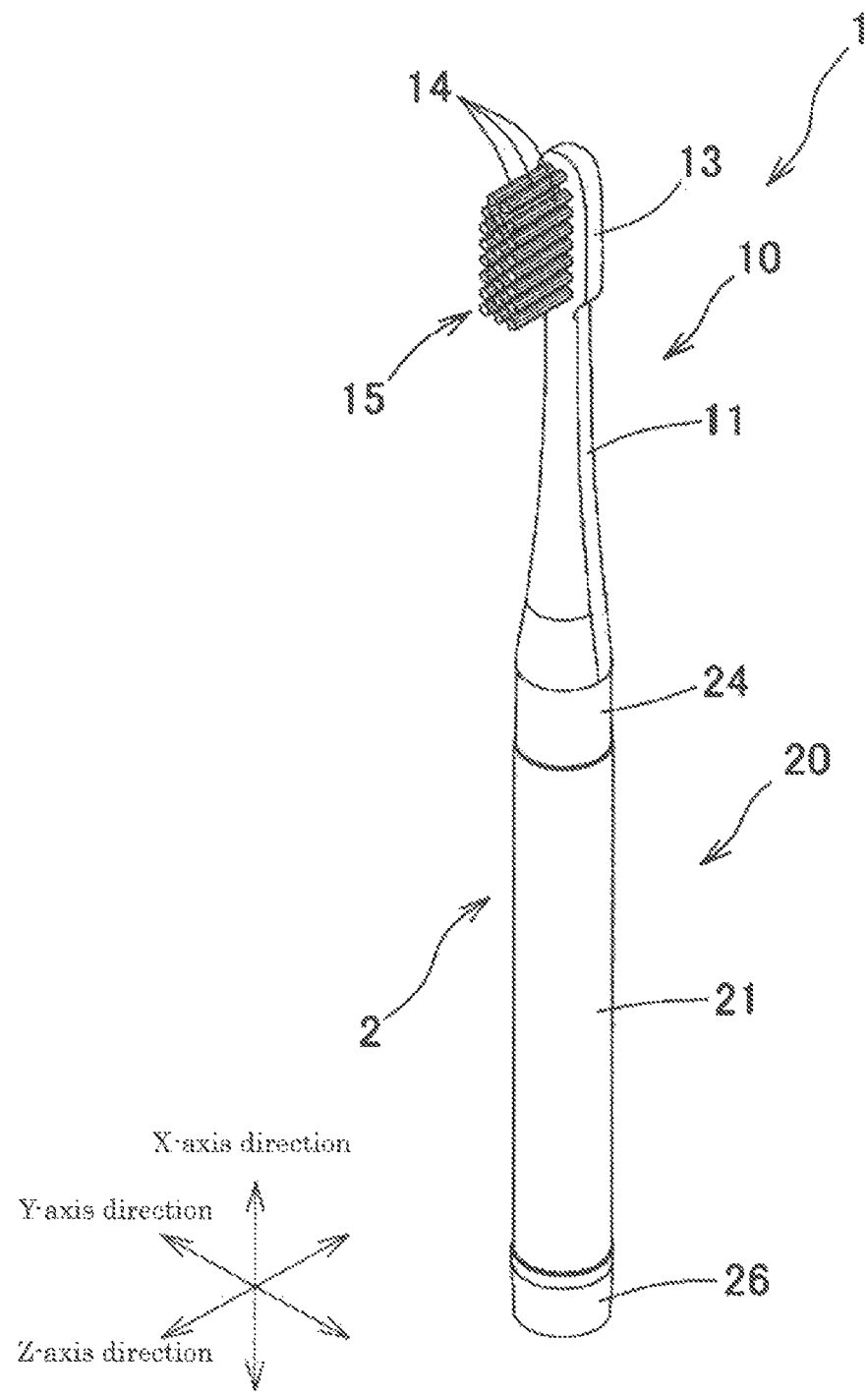
FIG. 1 is a perspective view of an electric toothbrush.
Figure 2:
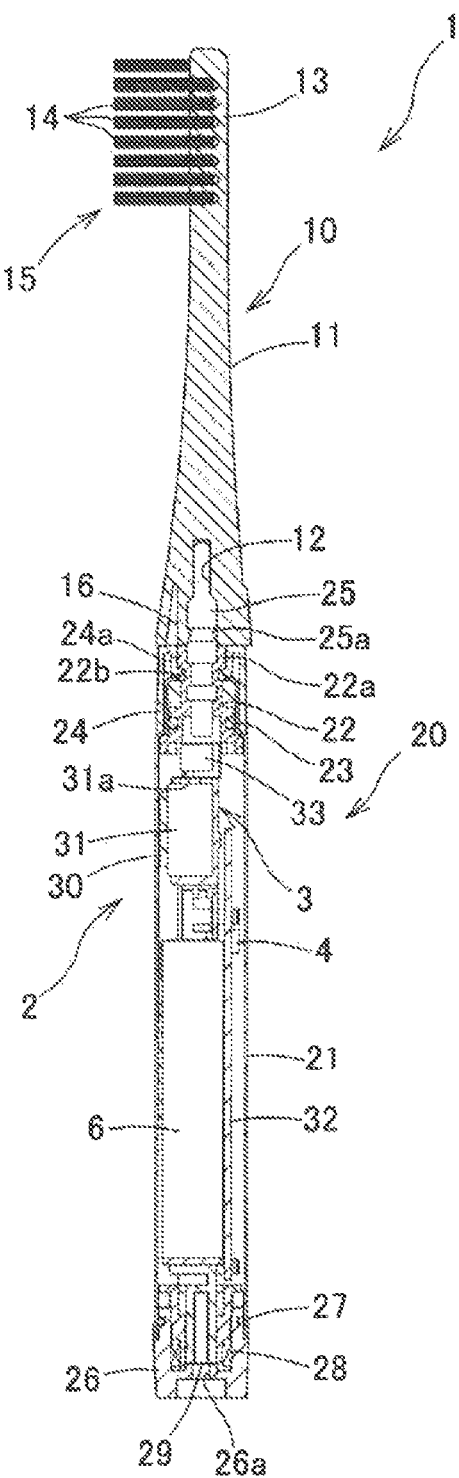
FIG. 2 is a vertical cross-sectional view of the electric toothbrush.
Figure 3:
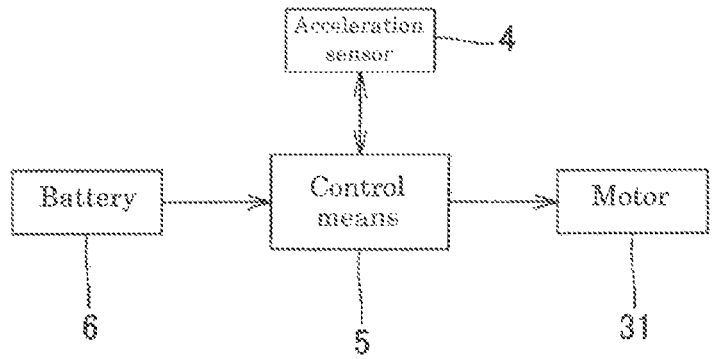
FIG. 3 is a block diagram of a control system in the electric toothbrush.

As illustrated in FIGS. 1 to 3, an electric toothbrush 1 includes: a toothbrush main body 2 having a brush part 15 and a handle part 20 for manually operating the brush part 15; a vibration generation means 3 that vibrates the brush part 15; an acceleration sensor 4 that detects a manual brushing action; a control means 5 that controls at least the vibration generation means 3 by switchover between the operating state and the stopped state according to the output from the acceleration sensor 4; and a battery 6 for driving the vibration generation means 3 and the control means 5.

The toothbrush main body 2 includes the handle part 20 and a replacement brush 10 detachably attached to the handle part 20. The replacement brush 10 has an implanting base 13 at the upper end portion of a haft 11. The implanting base 13 has a plurality of bristles 14 implanted therein. The plurality of bristles 14 forms the brush part 15.

The handle part 20 will be described. The handle part 20 has a cylindrical casing 21 of an almost circular cylinder shape or the like. An upper plug 22 is fitted in a water-tight manner into the upper end portion of the casing 21 via a seal ring 23. The upper plug 22 has at the upper end portion a cylindrical part 22$a$ protruding upward from the casing 21. A plug fixation member 24 is fitted onto the upper end portions of the cylindrical part 22a and the casing 21. The upper plug 22 and the plug fixation member 24 are attached to the upper end portion of the casing 21 by engaging a lock piece 24a of the plug fixation member 24 in a groove 22b of the cylindrical part 22a such that the upper plug 22 and the plug fixation member 24 do not fall off the casing 21. The upper plug 22 is provided with a coupling shaft 25 protruding upward and having the lower half portion embedded integrally into the central portion of the upper plug 22. The replacement brush 10 is detachably attached to the coupling shaft 25 by fitting the coupling shaft 25 into an attachment hole 12 at the lower end portion of the replacement brush 10. The upper plug 22 and the coupling shaft 25 may be formed as separate members or as an integral part.

The replacement brush 10 has an elastically deformable lock piece 16 constituting a circumferential portion of the attachment hole 12, and the coupling shaft 25 has an engagement groove 25a in the middle thereof. The replacement brush 10 is detachably attached by engagement between the lock piece 16 and the engagement groove 25a such that the replacement brush 10 hardly falls off by the power of a brushing action. However, the structure for coupling the replacement brush 10 to the coupling shaft 25 may be any known structure, for example, in which the coupling shaft 25 is inserted into the attachment hole 12 of the replacement brush 10 and then the replacement brush 10 is turned at a certain angle to couple the replacement brush 10 to the coupling shaft 25.

A lower plug 26 is provided at the lower end portion of the casing 21. The upper half portion of the lower plug 26 is fitted in a water-tight manner into the lower end portion of the casing 21 via a seal ring 27. An induction coil 28 is fitted into the lower plug 26 such that, when the electric toothbrush 1 is set on a battery charger not illustrated, an inductive current is generated in the induction coil 28 to charge the battery 6. The lower plug 26 has a degassing hole 26a in the lower wall portion such that, even when a gas is generated due to deterioration of the secondary battery, the generated gas can be discharged to the outside via the degassing hole 26a to prevent the toothbrush main body 2 from bulging, deforming, or rupturing. A breathable film 29 not letting a liquid pass but letting a gas pass is provided across the end portion of the degassing hole 26a inside the casing 21 to prevent foreign matter from the outside such as water from flowing into the electric toothbrush 1.

A support frame 30 is fitted into the casing 21 in an immovable manner. A motor 31 is attached to the upper portion of the support frame 30. The battery 6 is attached to the lower portion of the support frame 30. A circuit board 32 is attached to the side portion of the support frame 30. The motor 31, the battery 6, and the circuit board 32 are incorporated into the casing 21 together with the support frame 30.

Figure 13:
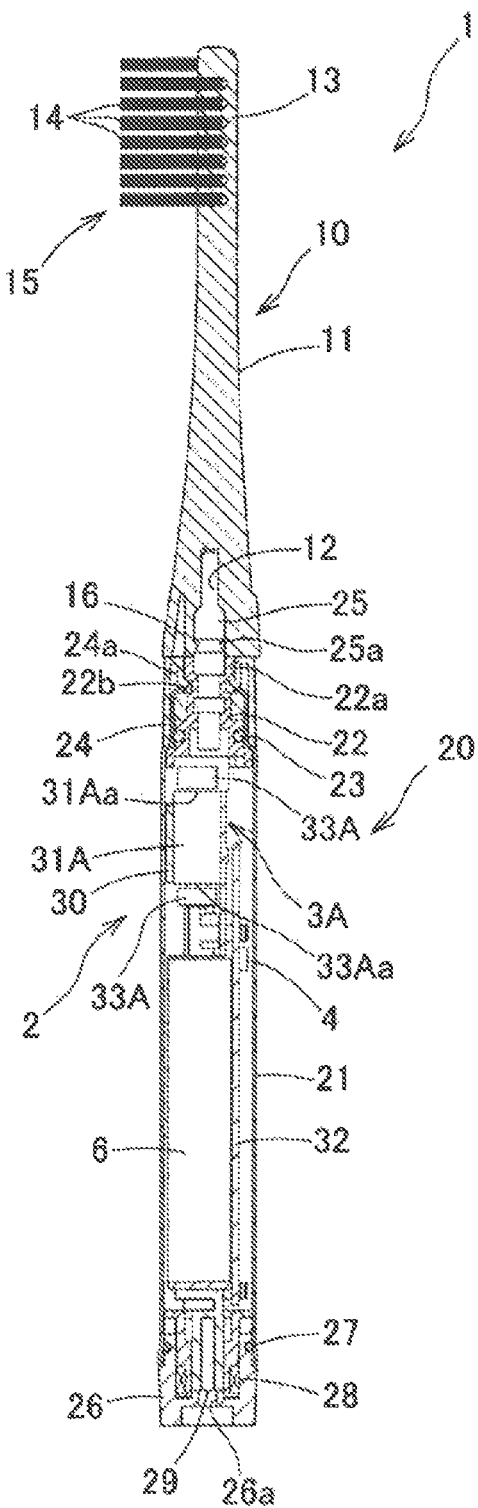
FIG. 13 is a vertical cross-sectional view of another electric toothbrush including a vibration generation means.

The vibration generation means 3 has the motor 31 and a weight 33 fixed to the upper end portion of a rotation shaft 31a of the motor 31 such that the motor 31 rotates eccentrically the weight 33 to vibrate the upper portion of the casing 21 and transfer the vibrations to the brush part 15 via the coupling shaft 25 and the haft. Alternatively, instead of the vibration generation means 3, a vibration generation means 3A may be used, including: a linear actuator 31A having an output shaft 31Aa reciprocating linearly along the length of the casing 21; and weights 33A fixed to the both end portions of the output shaft 31Aa of the linear actuator 31A, as illustrated in FIG. 13, such that the linear actuator 31A causes the weights 33A to reciprocate linearly to transfer the vibrations acting on the casing 21 to the brush part 15. In this case, a brushing action by Bass method can be assisted. The weight 33A may be provided only at one end.

The battery 6 driving the motor 31 and the control means 5 may be a primary battery. However, the battery 6 is preferably a secondary battery such as a nickel-hydride secondary battery or a lithium-ion secondary battery.

The circuit board 32 is provided with a charging circuit for charging the battery 6 by an inductive current supplied from the induction coil 28, the acceleration sensor 4 that detects motion of the handle part 20 along the length of the handle part 20 (the X-axis direction), the control means 5 for controlling power distribution to the motor 31 in response to the output from the acceleration sensor 4, and the like.

The control means 5 is mainly composed of a CPU, a RAM, and a ROM. The ROM of the control means 5 stores an operation control program for controlling operation of the motor 31 according to the output from the acceleration sensor 4.

Figure 4:
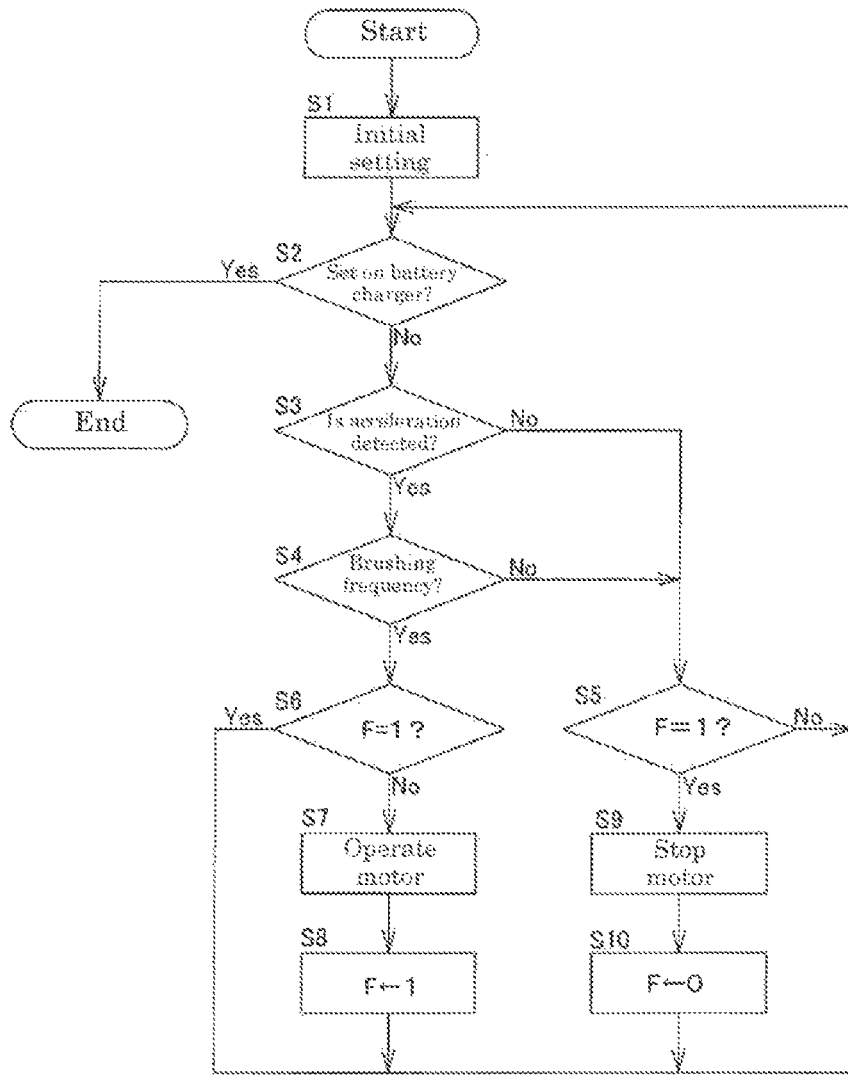
FIG. 4 is a flowchart of the control system in the electric toothbrush.

Next, the operation control program executed by the control means 5 will be described with reference to the flowchart described in FIG. 4. The control program is intended to switch the motor 31 between the operating state and the stopped state according to the output from the acceleration sensor 4. In FIG. 4, Si (i=1, 2, 3, . . . ) denote steps.

This control is started when the electric toothbrush 1 is detached from the battery charger and the induction coil 28 stops supply of an inductive current, and the acceleration sensor 4 is brought into the state capable of detecting the acceleration. At S1, necessary initial settings are made such as resetting a flag F. At S2, it is determined whether the electric toothbrush 1 is set on the battery charger or not by the presence or absence of the inductive current from the induction coil 28. In this embodiment, power is always distributed to the control means 5 and the acceleration sensor 4 regardless of whether the electric toothbrush 1 is attached to or detached from the battery charger. Alternatively, the electric toothbrush 1 may be configured such that, when the electric toothbrush 1 is detached from the battery charger and the induction coil 28 stops supply of an inductive current, power is distributed to the control means 5 and the acceleration sensor 4 to start this control, and when the electric toothbrush 1 is set on the battery charger and the induction coil 28 starts to supply an inductive current, power distribution to the control means 5 and the acceleration sensor 4 is stopped.

When the electric toothbrush 1 is detached from the battery charger to start tooth-brushing, it is determined as No at S2 and the process moves to S3 to determine whether acceleration is generated according to the output from the acceleration sensor 4. When it is determined that acceleration is generated according to the output from the acceleration sensor 4, the frequency of motion of the electric toothbrush is determined from the waveform output from the acceleration sensor 4. At S4, it is determined whether the frequency falls within the range of frequencies at the time of manual brushing, that is, whether the frequency falls within the range of 1 to 7 Hz. Specifically, the frequency of manual brushing in the X-axis direction is 1 to 2 Hz at lower speeds and 5 to 6 Hz at higher speeds. Accordingly, when the frequency of the waveform output from the acceleration sensor 4 falls within the range of 1 to 7 Hz, it is determined that the user is performing a manual brushing action.

After detaching the electric toothbrush 1 from the battery charger, the user may wash the brush portion 15, put toothpaste on the brush part 15, and if necessary, place the electric toothbrush 1 temporarily on the washstand until starting actually tooth-brushing. When the user washes the brush part 15 and puts toothpaste on the brush part 15, the frequency output from the acceleration sensor 4 is different from the frequency at a manual brushing action and thus it is determined as No at S4. When the user places the electric toothbrush 1 temporarily on the washstand, the acceleration is determined as zero from the output from the acceleration sensor 4, and thus it is determined as No at S3 and the process moves to S5. At S5, it is determined whether the flag F is set. Since the flag F is reset as an initial setting, it is determined as No at S5 and the process returns to S2. Steps S2, S3, and S5 or S2 to S5 are repeated until the user actually starts a manual brushing action.

When the user puts the brush part 15 into his/her mouth and starts a brushing action, it is determined as Yes at S4 and then it is determined whether the flag F is in the state of F=1 (S6). Since the flag F is reset as an initial setting at the beginning of a tooth-brushing action, the process moves to S7 to activate the motor 31 to rotate the weight 33 to vibrate the brush part 15. At S8, the flag F is set and then the process returns to S2.

As described above, when the user starts a manual brushing action, the motor 31 is activated and the flag F is set. Accordingly, when the process moves to S6 next time through S2 to S4, it is determined as Yes at S6 and the process returns to S2. While the user is performing a manual brushing action, steps S2 to S4 and S6 are repeated to assist the manual brushing action by the vibration generation means 3.

Then, when the user completes tooth-brushing and stops the brushing action, it is determined as No at S3 or S4 and the process moves to S5. Since the flag F is set, it is determined as Yes at S5. The motor 31 is stopped at S9, and the flag F is reset at S10, and then the process returns to S2. Then, after the stoppage of the motor 31, the user takes the brush part 15 out of the mouth, washes the brush part 15 with water, and set the electric toothbrush 1 on the battery charger. Until the user sets the electric toothbrush 1 on the battery charger, steps S2, S3, and S5 or S2 to S5 are repeated to keep the motor 31 in the stopped state, as in the case of waiting until the user actually starts tooth-brushing as described above.

Then, when the user completes tooth-brushing and sets the electric toothbrush 1 on the battery charger, it is determined as Yes at S2 and the control means 5 terminates the control. As a result, the acceleration sensor 4 stops the detection of acceleration. In the foregoing case, it is necessary to distribute power to the control means 5 and the acceleration sensor 4 regardless of whether the electric toothbrush 1 is set on the battery charger or not. However, providing the electric toothbrush 1 with an additional function of powering on and off would eliminate the need for power distribution to the control means 5 and the acceleration sensor 4. Accordingly, by turning off power supply to these components, it is possible to reduce standby electricity in the electric toothbrush 1 as much as possible.

According to the electric toothbrush 1, when the user operates a manual brushing action with the toothbrush main body 2, the acceleration sensor 4 detects the acceleration during the brushing action, the control means 5 switches the vibration generation means 3 to the operating state, and the vibration generation means 3 provides vibrations to the brush part 15, thereby to allow the user to brush the teeth with a motor-driven vibration assistance in the manual brushing action. Meanwhile, when the user stops the manual brushing action with the toothbrush main body 2, the control means 5 switches the vibration generation means 3 to the stopped state according to the output from the acceleration sensor 4.

As described above, the electric toothbrush 1 is configured based on the assumption that the user performs a manual brushing action, and thus the motor 31 of the vibration generation means 3 can be of a small size with relatively weak power. Accordingly, the outer diameter of the handle part 20 of the electric toothbrush 1 can be set to, for example, 8 to 18 mm, preferably 8 to 15 mm, more preferably 8 to 12 mm to make the handle part 20 thin and slim. Accordingly, it is possible to realize the electric toothbrush suited to a manual brushing action with the slim handle part 20 and the small-sized motor 31 of the vibration generation means 3 with relatively weak power, thereby to enhance the ease of the manual brushing action and provide significant brushing performance. In addition, the vibration generation means 3 can be operated by performing a manual brushing action with the toothbrush main body 2, and the vibration generation means 3 can be stopped by discontinuing the manual brushing action with the toothbrush main body 2, and the degree of assistance can be automatically determined or changed according to the state of the brushing action. Accordingly, even when elderly persons with a weak feeling of fingers, sick persons and handicapped persons, and women with long and artificial nails brush their teeth or when caregivers brush the teeth of persons in need of care or infants instead of them, they can easily switch the vibration generation means 3 between the operating state and the stopped state. Further, the degree of assistance in brushing can be automatically changed according to the state of a brushing action to control a more effective and correct brushing state. The electric toothbrush 1 does not need a mechanical power switch and thus the handle part 20 of the electric toothbrush 1 can be made further thinner and slimmer with reduced asperities on the outer surface to improve the cleaning performance of the handle part 20. In addition, the electric toothbrush 1 can be formed of a simplified water-tight structure to improve water tightness and reduce the costs for producing the electric toothbrush 1. Furthermore, the vibration generation means 3 can be operated by performing a manual brushing action in the state where toothpaste is put on the brush part 15 and the brush part 15 is inserted into the mouth. This prevents the toothpaste from falling or dispersing. Even if the battery 6 becomes out of charge, the electric toothbrush 1 can be used for tooth-brushing as a manual toothbrush.

The acceleration sensor 4 is not limited to the acceleration sensor 4 detecting the acceleration in the X-axis direction. As illustrated in FIG. 1, an acceleration sensor detecting the acceleration in the Y-axis direction orthogonal to the length of the handle part 20 in a plane including the implanting base 13 and an acceleration sensor detecting the acceleration in the Z-axis direction orthogonal to the plane including the implanting base 13 may be provided, such that the motor 31 of the vibration generation means 3 can be switched between the operating state and the stopped state according to the outputs from these acceleration sensors. In this configuration, however, the sensor control would be complicated and thus the only two acceleration sensors in the X-axis and Y-axis directions may be preferably used. Even in this case, the electric toothbrush is applicable to various brushing methods such as scrub method, horizontal method, Bass method, vertical method, and Fones method. Nevertheless, by providing only the acceleration sensor 4 detecting the acceleration in the X-axis direction as in this embodiment, it is possible to detect reliably brushing actions by Bass method and scrub method that are the most recommended brushing methods for the reason discussed below.

FIGS. 11(a) and 11(b) describe the outputs from the acceleration sensor 4 detecting the acceleration in the X-axis direction in the case (a) where a manual brushing action is performed at 2 Hz and in the case (b) where a manual brushing action is performed at 6 Hz, during stoppage of the motor 31 by Bass method or scrub method, respectively. FIGS. 12(a) and 12(b) describe the outputs from an acceleration sensor detecting the acceleration in the Y-axis direction under the same brushing conditions as described above, respectively. FIGS. 12(c) and 12(d) describe the outputs from an acceleration sensor detecting the acceleration in the Z-axis direction under the same brushing conditions as described above, respectively. It can be understood from these graphs that, in the case of tooth-brushing by Bass method or scrub method, the hand is mainly reciprocated in the X-axis direction, and the outputs from the acceleration sensor 4 detecting the acceleration in the X-axis direction are significantly larger than the outputs from the acceleration sensors in the Y-axis and the Z-axis directions. Therefore, it is possible to detect reliably a brushing action by Bass method or scrub method only by the acceleration sensor 4 detecting the acceleration in the X-axis direction.

FIGS. 11(c) and 11(d) describe the outputs from the acceleration sensor 4 detecting the acceleration in the X-axis direction in the case where a manual brushing action is performed at 2 Hz and in the case where a manual brushing action is performed at 6 Hz by Bass method or scrub method during operation of the motor 31, respectively. It can be understood from these graphs that the acceleration sensor 4 is influenced by the vibrations of the motor 31. Accordingly, it is preferred to provide a filter circuit as necessary to remove a vibration component caused by the motor 31 from the outputs from the acceleration sensor 4, for the purposes of enhancing detection accuracy and preventing malfunction.

Next, descriptions will be given as to other embodiments with partial modifications made to the configuration of a control system of the electric toothbrush 1. The following embodiments (1) to (5) may be combined in an arbitrary manner.

(1) The vibration generation means 3 can be stopped when an abnormal operation of the electric toothbrush 1 is detected according to the output from the acceleration sensor 4.

Figure 5:
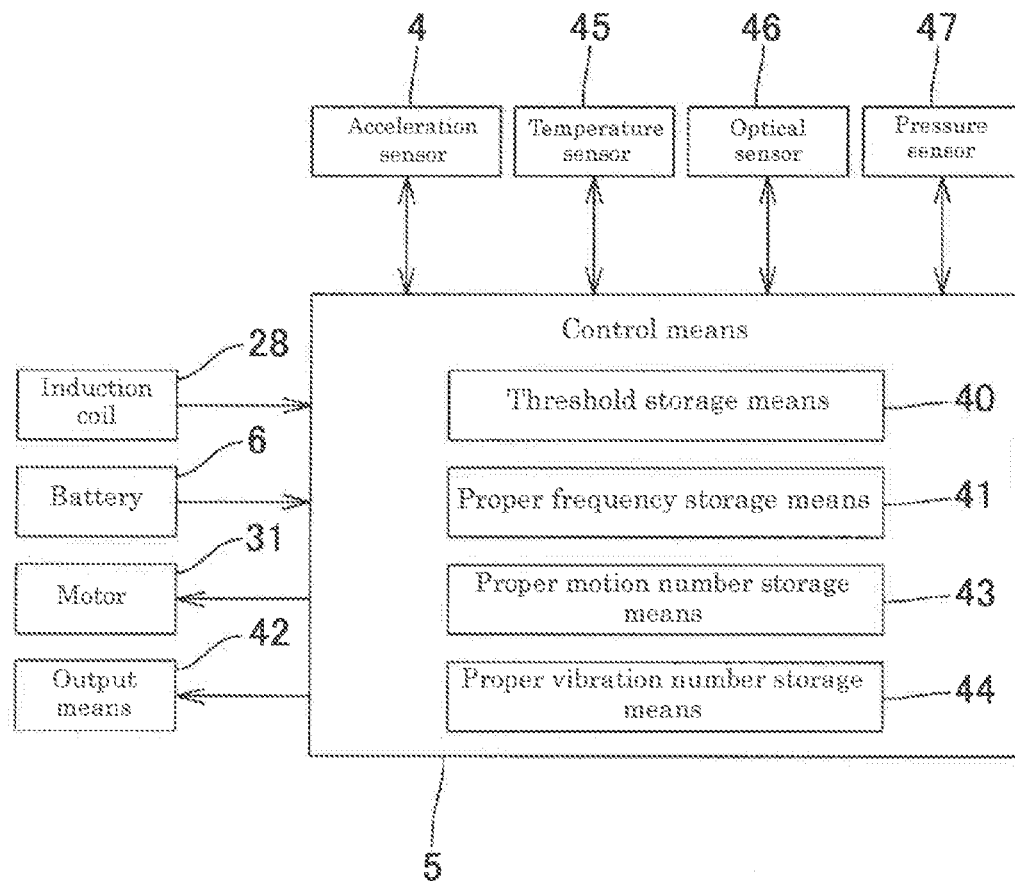
FIG. 5 is a block diagram of a control system in another electric toothbrush.
Figure 6:
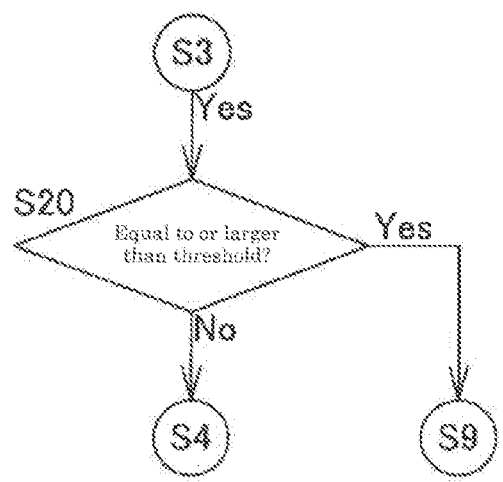
FIG. 6 is a flowchart of the control system for forcibly stopping a motor.

Specifically, as illustrated in FIG. 5, the control means 5 includes a threshold storage means 40 that stores in advance a threshold larger than the upper limit for the output from the acceleration sensor 4 during a manual brushing action, thereby to add S20 described in FIG. 6 to S1 to S11 described in FIG. 4.

In this case, as described in FIGS. 4 and 6, when the output from the acceleration sensor 4 is detected and it is determined as Yes at S3, it is then determined at S20 whether the output from the acceleration sensor 4 is equal to or larger than the threshold. When the output is smaller than the threshold, the process moves to S4 to perform the same control as that in the foregoing embodiment. When the output is equal to or larger than the threshold, the process moves to S9 to stop the motor 31, and then the flag F is reset at S10. That is, during a normal tooth-brushing action or any other action involved in the tooth-brushing action such as putting toothpaste on the brush part 15, placing the electric toothbrush 1 on the washstand, or performing a manual brushing action, the output from the acceleration sensor 4 is small and thus it is determined as No at S20, and the process moves to S4 to perform the same control as that in the foregoing embodiment. When the output is equal to or larger than the threshold, the motor 31 is brought into emergency stop. For example, when any abnormal event occurs such as an inability to stop the motor 31, the user strongly shakes the electric toothbrush 1 to bring the motor 31 into an emergency stop. When the hard-material portion of the toothbrush main body 2 collides against the teeth during a brushing action, the acceleration sensor 4 detects the impact of the collision to switch the motor 31 temporarily to the stopped state.

(2) The number and direction of vibrations and the amplitude of the vibration generation means 3 can be controlled according to the output from the acceleration sensor 4.

Figure 7:
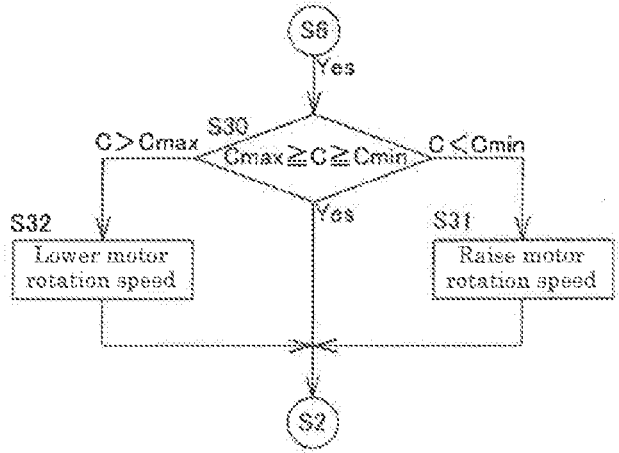
FIG. 7 is a flowchart of the control system for controlling motor revolutions according to a brushing frequency.

Specifically, as illustrated in FIG. 5, the control means 5 includes a proper frequency storage means 41 for storing in advance an upper limit Cmax and a lower limit Cmin for a brushing frequency C during a proper manual brushing action, thereby to add S30 to S32 described in FIG. 7 to S1 to S11 described in FIG. 4. The upper limit Cmax and the lower limit Cmin are frequencies calculated from variations in acceleration detected by the acceleration sensor 4 during a manual brushing action, and are specifically set within the range of 1 to 7 Hz. For example, the upper limit Cmax may be set to 5 Hz and the lower limit Cmin to 3 Hz, which fall within the range of average brushing frequencies with healthy persons.

In this case, when it is determined as Yes at S6, it is then determined at S30 whether the brushing frequency C falls within the proper range according to the frequency output from the acceleration sensor 4. When the brushing frequency C falls within the proper range, the process moves to S2 to perform the same control as the foregoing one. When the brushing frequency C is smaller than the lower limit Cmin, the rotation speed of the motor 31 is raised (S31) to increase the motor-driven vibrations of the brush part 15, and then the process moves to S2. When the brushing frequency is high beyond the upper limit Cmax, the rotation speed of the motor 31 is lowered (S32) to decrease the motor-driven vibrations of the brush part 15, and then the process moves to S2. This allows the user to brush the teeth by uniform brushing power. In contrast to the foregoing cases, the control may be performed in cooperation with the manual brushing power such that the rotation speed of the motor 31 is lowered when the power of a manual brushing action is weak and the acceleration is low, and the rotation speed of the motor 31 is raised when the power of a manual brushing action is strong and the acceleration is high. Further, the electric toothbrush 1 may include a posture detection part that detects the posture of the electric toothbrush, such as a geomagnetic sensor, a gyro sensor, or a triaxial acceleration sensor such that the control means 5 stores in advance the output from the posture detection part indicating the postures of proper manual brushing by each of the Bass method, scrub method, rolling method, and Fones method, the output from the posture detection part during the user's actual tooth-brushing is analyzed, and the user is guided to a brushing action by a correct method through audio output or the like, and the number and direction of vibrations and amplitude of the vibration generation means 3 are controlled to determine the degree of assistance and/or the method of assistance.

(3) It is possible to instruct the user on the correct brushing method according to the output from the acceleration sensor 4.

Figure 8:
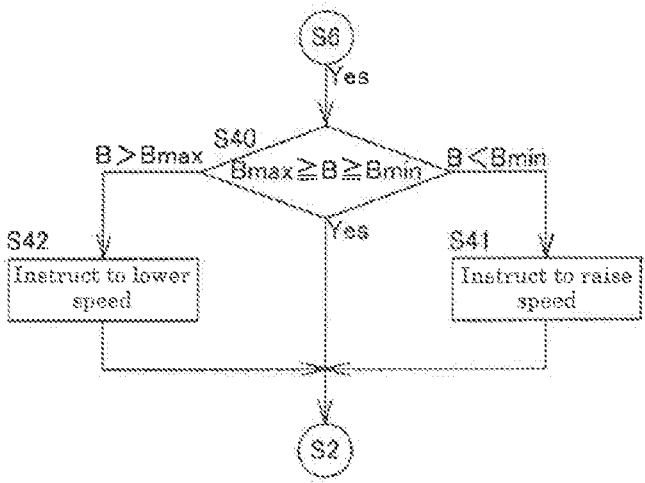
FIG. 8 is a flowchart of the control system for instructing on a brushing method.

Specifically, as illustrated in FIG. 5, the electric toothbrush 1 is provided with an output means 42 for providing the user with instructive brushing information by audio or display, and the control means 5 includes a proper motion number storage means 43 for storing in advance an upper limit Bmax and a lower limit Bmin for the number of reciprocations per minute (brushing frequency) B during a proper manual brushing action, thereby to add S40 to S42 described in FIG. 8 to S1 to S11 described in FIG. 4.

In this case, when it is determined as Yes at S6, it is then determined at S40 whether the number of reciprocations per minute (brushing frequency) B during a manual brushing action is a proper number. When the number of reciprocations per minute (brushing frequency) B is a proper number, it is determined that the user is performing a manual brushing action by a correct brushing method, and the process moves to S2 to perform the same control as that in the foregoing embodiment. When the number of reciprocations per minute (brushing frequency) B is smaller than the lower limit Bmin, the user is instructed to increase the brushing speed (S41) and the process moves to S2. When the number of reciprocations per minute (brushing frequency) B is larger than the upper limit Bmax, the user is instructed to decrease the brushing speed (S42), and the process moves to S2.

(4) It is possible to inform the user whether the vibration generation means 3 in operating normally according to the output from the acceleration sensor 4.

Figure 9:
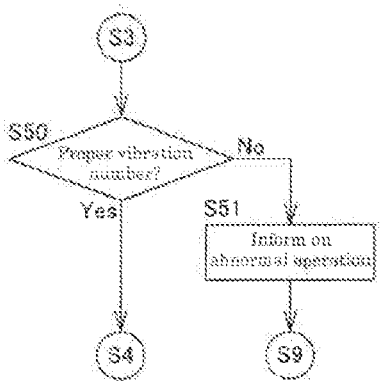
FIG. 9 is a flowchart of the control system for informing malfunction of the electric toothbrush.

Specifically, as illustrated in FIG. 5, the electric toothbrush 1 is provided with the output means 42 for providing the user with information on operation of the vibration generation means 3 by audio or display, and the control means 5 includes a proper vibration number storage means 44 for measuring and storing in advance the number of vibrations of the motor 31 in the normal operation state, thereby to add S50 and S51 described in FIG. 9 to S1 to S11 described in FIG. 4.

When the acceleration is detected in the output from the acceleration sensor 4 and it is determined as Yes at S3, the process moves to S50 to determine whether the frequency determined from variations in acceleration indicated by the output from the acceleration sensor 4 falls within the range of frequencies indicating proper operation of the motor 31. When the determined frequency falls within the range of proper frequencies, the motor 31 is normally operating, and thus the process moves to S4 to perform the same control as that in the foregoing embodiment. When the determined frequency does not fall within the range of proper frequencies, the user is informed through the output means 42 that the battery 6 of the electric toothbrush 1 is out of charge or the motor 31 is malfunctioning.

(5) It is possible to control the operating state of the vibration generation means 3 using the acceleration sensor 4 and other sensors in combination.

Specifically, as illustrated in FIG. 5, a temperature sensor 45 is provided at the handle part 20 to detect whether the user holds the handle part 20 of the electric toothbrush 1 by hand, and an optical sensor 46 is provided at the portion of the handle part 20 covered by the replacement brush 10, for example, the coupling shaft 25 or the portion near the coupling shaft 25 to detect whether the replacement brush 10 is attached to the handle part 20 for tooth-brushing, and a pressure sensor 47 is provided at the brush part 15 to detect a pressure acting on the brush part 15 and determine whether the user is performing a brushing action. The motor 31 can be controlled according to the outputs from one or two or more selected from among these sensors 45 to 47 and the acceleration sensor 4. This configuration allows the higher-accuracy detection on whether the user is performing a manual brushing action.

Figure 10:
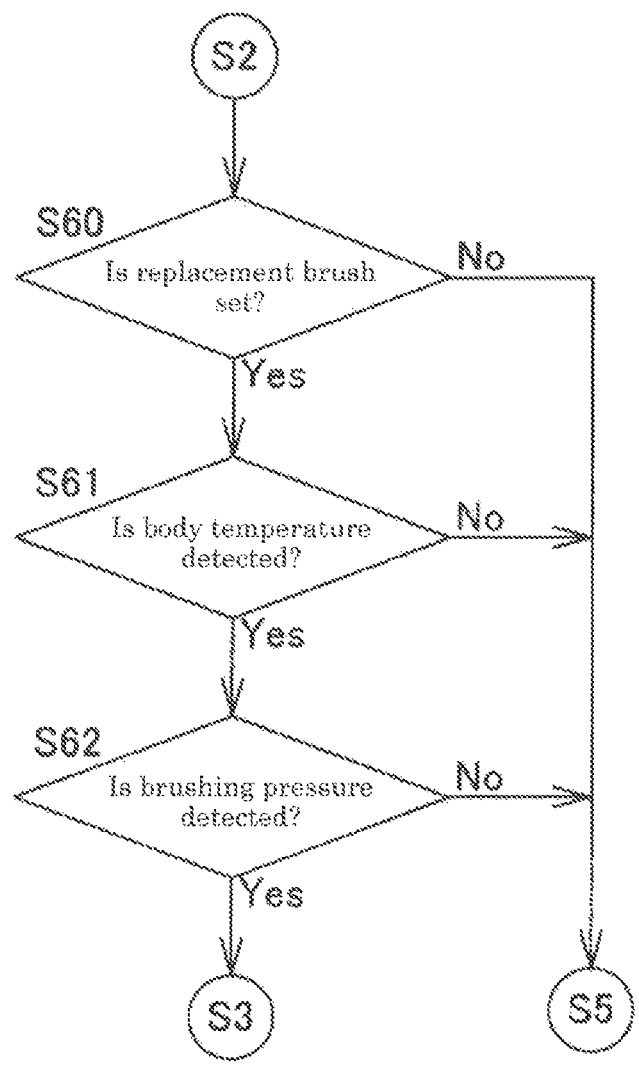
FIG. 10 is a flowchart of the control system for using an acceleration sensor and other sensors in combination.

As described in FIG. 10, when it is determined as Yes at S2, the process moves to S60 to determine whether the replacement brush 10 is attached to the handle part 20 according to the output from the optical sensor 46. When it is determined as Yes, the temperature sensor 45 detects the body temperature to determine whether the handle part 20 is held by the user's hand. When it is determined as Yes, it is then determined whether the user is performing a brushing action according to the output from the pressure sensor 47. When it is determined as Yes at S60 to S62, S3, and S4, the user is performing a brushing action and thus the process moves to S6. When it is determined as No at any of S60 to S62, S3, and S4, the user is not performing a brushing action and thus the process moves to S5. When it is determined as No at any of S60 to S62, S3, and S4, the motor 31 is stopped. Accordingly, it is possible to prevent the electric toothbrush 1 from malfunctioning due to vibrations caused during distribution and storage of the electric toothbrush 1 after the shipment or when the user carrying the electric toothbrush 1 is riding in an automobile or the like. The electric toothbrush 1 may also be controlled by the use of the acceleration sensor in combination with any of other sensors such as a geomagnetic sensor, a gyro sensor, a pressure sensor, a load sensor, a temperature sensor, and an optical sensor.

In this embodiment, the start and end of the control are decided depending on whether the electric toothbrush 1 is set on the battery charger, that is, whether an inductive current is provided by the induction coil 28. Preferably, the electric toothbrush 1 may be configured to include a small-sized power generator capable of generating power by a brushing action, so that the control of the electric toothbrush 1 is started with power generation by the power generator as a trigger, and then the control of the electric toothbrush 1 is stopped after a lapse of a certain period of time since stoppage of the power generation. Specifically, when the electric toothbrush 1 is detached from the battery charger, the operation of the motor 31 is stopped but power distribution to the control means 5 is continued. This configuration preferably prevents the situation in which the motor 31 cannot be activated as needed when the battery 6 becomes exhausted due to the standby electricity. In addition, this configuration preferably shuts off power distribution to the control means 5 and the acceleration sensor 4 until the user starts a brushing action, thereby to reduce the standby electricity.

According to the electric toothbrush 1, the acceleration sensor 4 and the computation part of the control means 5 are both energized during battery charging. Alternatively, the electric toothbrush 1 may be configured such that the computation part is in the sleep state and the acceleration sensor 4 is in the standby state to minimize power consumption during battery charging. Since the electric toothbrush 1 uses the secondary battery 6 as a power source, the final discharge voltage of the secondary battery 6 may be preset in the control means 5 such that, when the voltage of the secondary battery 6 is equal to or lower than the final discharge voltage, the discharge of the secondary battery 6 is disabled to preferably prevent performance degradation due to over discharge of the secondary battery 6. By setting the final discharge voltage, when the voltage falls below the final discharge voltage, the power supply from the secondary battery 6 is discontinued to shut off power distribution to the acceleration sensor 4, the computation part of the control means 5, the field-effect transistor, and others, and stop completely the control of the electric toothbrush 1. To recover the functions of the electric toothbrush 1 from this state, it is preferred that, with putting the electric toothbrush 1 on the battery charger as a trigger, an inductive current is generated in the induction coil 28 included in the electric toothbrush 1 and a voltage prescribed by the field-effect transistor and the regulator is applied to the computation part and others.

Next, other embodiments with partial modifications to the lower structure of the electric toothbrush 1 will be described. The same components in the following embodiments as those in the foregoing embodiment will be given the same reference signs as those in the foregoing embodiment, and descriptions thereof will be omitted.

(1) As illustrated in FIGS. 14(*a*) and 14(*b*), the electric toothbrush 1 may be configured such that a lower structure 50 includes: instead of the lower plug 26, a lower plug 54 having a plug main body 52 with an L-shaped cutout 51 and a transparent member 53 fitted and fixed to the cutout 51; and an LED 55 on the circuit board 32 opposed to the transparent member 53 to display the operating states of the electric toothbrush 1 and the battery charger, so that the user can visually check the lighting state of the LED 55 through the transparent member 53. The LED 55 may emit light in a single color or a plurality of switchable colors to inform the user of the states of the electric toothbrush 1 and the battery charger. For example, two LEDs emitting green light and red light may be provided so that the green LED is on when the secondary battery 6 is sufficiently charged, and blinks when the secondary battery becomes weak, and turns off when the secondary battery 6 falls below the final discharge voltage, whereas the red LED turns on when the electric toothbrush 1 is set on the battery charger to charge the secondary battery 6, and the red LED may remain in the off state even though the electric toothbrush 1 is set on the battery charger to inform the user that the battery charger may be defective. In FIGS. 14(*a*) and 14(*b*), reference sign 56 denotes a battery contact connected to the minus pole of the secondary battery 6, and reference sign 57 denotes a cutout for rotation stoppage formed at the lower end portion of the casing 21. When the transparent member 53 fits to the cutout 57, the relative rotation of the casing 21 and the lower plug 54 is controlled.

(2) As illustrated in FIGS. 15(*a*) and 15(*b*), the electric toothbrush 1 may be configured such that a lower structure 60 includes: instead of the lower plug 26, a lower plug 67 having a plug main body 62 with a square hole 61 formed on the outer peripheral surface of a middle portion along the height, a transparent member 63 fitted and fixed to the square hole 61, an attachment hole 64 formed on the bottom surface, and a seal ring 65 and a push button 66 fitted into the attachment hole 64; the LED 55 on the circuit board 32 as in the lower structure 50 to display the operating states of the electric toothbrush 1 and the battery charger so that the user can visually check the lighting state of the LED 55 through the transparent member 63; and a main power switch 68 at the lower end portion of the circuit board 32 so that the user can operate the main power switch 68 by the push button 66 via an operation member 69 to switch the malfunction prevention function of shutting off power distribution to the acceleration sensor 4 and others between the on state and the off state. This configuration produces the same advantages as those of the lower structure 50. In addition, according to this configuration, during distribution and storage of the electric toothbrush 1 after the shipment or when the user carrying the electric toothbrush 1 is riding in an automobile or the like, the push button 66 can be operated to turn on the malfunction prevention function by the main power switch 68 to shut off power distribution to the acceleration sensor 4 and others, thereby to prevent reliably the electric toothbrush 1 from malfunctioning due to vibrations acting on the electric toothbrush 1. Further, in this configuration, no standby electricity is generated to prevent reduction in operating time of the electric toothbrush 1. Unlike the conventional power switch, the main power switch 68 does not need to be operated during use of the electric toothbrush 1 and thus can be provided at a position where the user cannot operate while holding the electric toothbrush 1, that is, at the lower end of the handle part 20 as illustrated in FIGS. 15(*a*) and 15(*b*). The provision of the main power switch 68 eliminates the need to make the handle part 20 of the electric toothbrush 1 thicker. During the use of the electric toothbrush 1, the push button 66 can be pressed again to turn off the malfunction prevention function by the main power switch 68, thereby switching the electric toothbrush 1 to the operating state.

Figure 16:
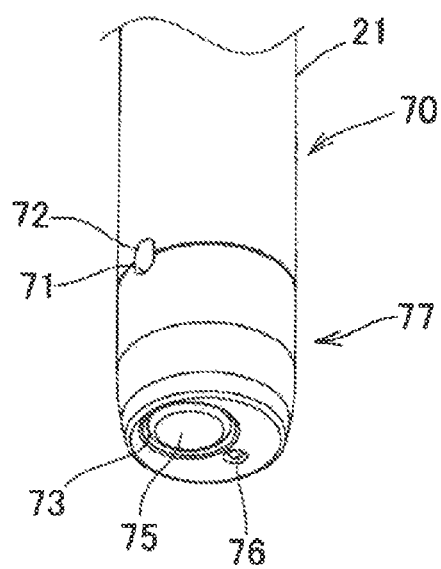
FIG. 16($a$) is a perspective view of a lower structure of another electric toothbrush and FIG. 16($b$) is a vertical cross-sectional view of the same.
Figure 16:
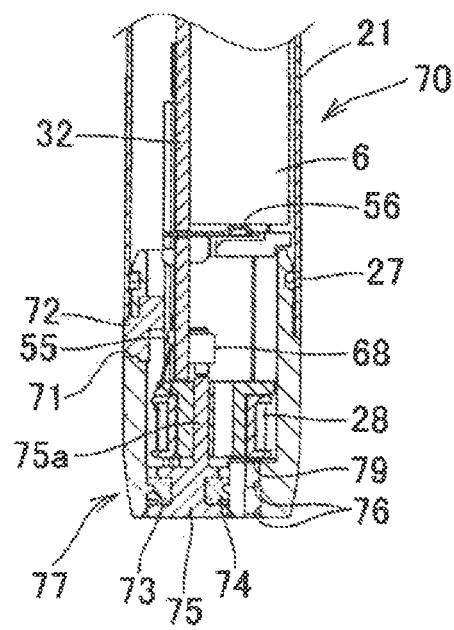
Figure 17:
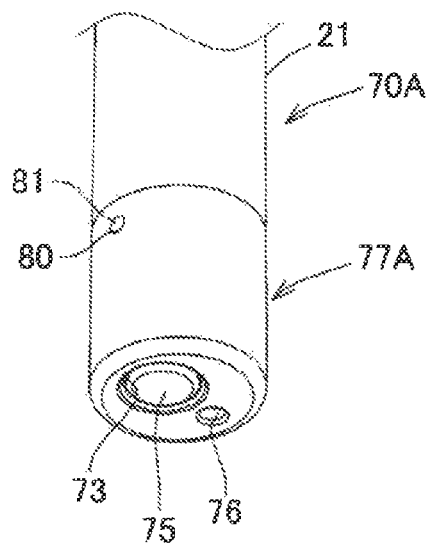
FIG. 17($a$) is a perspective view of a lower structure of another electric toothbrush and FIG. 17($b$) is a vertical cross-sectional view of the same.
Figure 17:
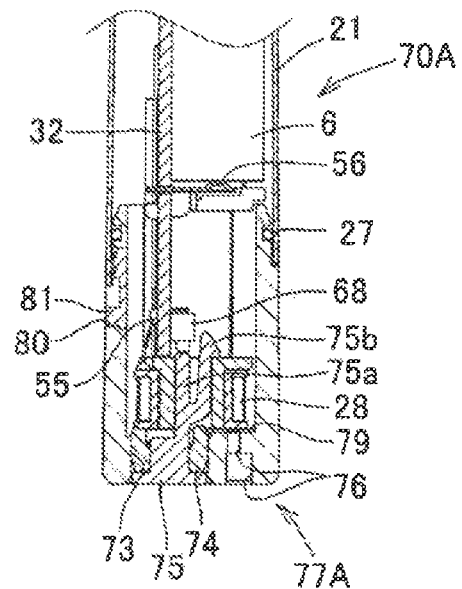

(3) As illustrated in FIGS. 16(*a*) and 16(*b*), the electric toothbrush 1 may be configured such that a lower structure 70 includes: instead of the lower plug 26, a lower plug 77 having an oval hole 71 formed on the outer peripheral surface of the middle part along the height, a transparent member 72 fitted and fixed to the oval hole 71, an attachment hole 73 formed on the bottom surface, a seal ring 74 and a push button 75 fitted into the attachment hole 73, and a degassing hole 76 formed on the bottom surface; the LED 55 on the circuit board 32 as in the lower structure 60 to display the operating states of the electric toothbrush 1 and the battery charger so that the user can visually check the lighting state of the LED 55 through the transparent member 72; the main power switch 68 at the lower end of the circuit board 32 so that the user can operate the main power switch 68 via an operation part 75*a* of the push button 75; and a breathable film 79 not letting a liquid pass but letting a gas pass at the inner end portion of the casing 21 in the degassing hole 76 to prevent foreign matter from the outside such as water from flowing into the electric toothbrush 1. This configuration produces the same advantage as those of the lower structure 60. In addition, according to this configuration, even if a gas is generated due to degradation of the secondary battery 6, the gas is discharged to the outside through the degassing hole 76 to prevent the electric toothbrush 1 from bulging, deforming, and rupturing. Alternatively, as illustrated in FIGS. 17(*a*) and 17(*b*), the electric toothbrush 1 may be configured such that a lower structure 70A includes a lower plug 77A having a round hole 80, instead of the oval hole 71, so that a transparent member 81 is fitted and fixed to the round hole 80, and a drop prevention hook 75*b* at the push button 75.

In this embodiment, the present invention is applied to the weight vibration-type electric toothbrush 1. Similarly, the present invention is also applicable to the linear motion-type, inverse motion-type, and linear vibration-type electric toothbrushes 1.

The embodiments of the present invention have been described so far. However, the present invention is not limited to the foregoing embodiments but can be modified without deviating from the gist of the present invention.

REFERENCE SIGNS LIST

1 Electric toothbrush
2 Toothbrush main body
3 Vibration generation means
4 Acceleration sensor 5 Control means
6 Battery
10 Replacement brush
11 Haft
12 Attachment hole
13 Implanting base
14 Bristle
15 Brush part
16 Lock piece
20 Handle part
21 Casing
22a Upper plug
22a Cylindrical part
22b Groove
23 Seal ring
24 Plug fixation member
24a Lock piece
25 Coupling shaft
25a Engagement groove
26 Lower plug
26a Degassing hole
27 Seal ring
28 Induction coil
29 Breathable film
30 Support frame
31 Motor
31a Rotation shaft
32 Circuit board
33 Weight
3A Vibration generation means
31A Linear actuator
31Aa Output shaft
33A Weight
40 Threshold storage means
41 Proper frequency storage means
42 Output means
43 Proper motion number storage means
44 Proper vibration number storage means
45 Temperature sensor
46 Optical sensor
47 Pressure sensor
50 Lower structure
51 Cutout
52 Plug main body
53 Transparent member
54 Lower plug
55 LED
56 Battery contact
57 Cutout
60 Lower structure
61 Square hole
62 Plug main body
63 Transparent member
64 Attachment hole
65 Seal ring
66 Push button
67 Lower plug
68 Main power switch
69 Operation member
70 Lower structure
71 Oval hole
72 Transparent member
73 Attachment hole
74 Seal ring
75 Push button
75a Operation part
76 Degassing hole
77 Lower plug
79 Breathable film
70A Lower structure
75b Hook
77A Lower plug
80 Round hole
81 Transparent member

The invention claimed is:

1. An electric toothbrush comprising:
   a toothbrush main body having a brush part and a handle part for manually operating the brush part;
   a vibration generation means that vibrates the brush part;
   an acceleration sensor that detects a manual brushing action; and
   a control means that controls the vibration generation means to switch between an operating state and a stopped state, according to output from the acceleration sensor, so that the vibration generation means is switched from the stopped state to the operating state at least when the toothbrush main body is moved in a manner of the manual brushing action, and the vibration generation means is switched from the operating state to the stopped state when the manual brushing action is stopped.

2. The electric toothbrush according to claim 1, wherein the vibration generation means includes a motor and a weight eccentrically rotated by the motor.

3. The electric toothbrush according to claim 1, wherein the acceleration sensor detects the motion of the toothbrush main body in an X-axis direction along the length of the toothbrush main body.

4. The electric toothbrush according to claim 1, wherein
   a threshold storage means is provided to store in advance a threshold larger than the upper limit for the output from the acceleration sensor during a manual brushing action, and
   when the output from the acceleration sensor is equal to or larger than the threshold stored in the threshold storage means, the control means switches the vibration generation means to the stopped state.

5. The electric toothbrush according to claim 1, wherein the control means controls the number of vibrations from the vibration generation means according to the output from the acceleration sensor.

6. The electric toothbrush according to claim 1, wherein
   an output means is provided to output information to the user, and
   the control means determines whether the user is performing a proper brushing action according to the output from the acceleration sensor, and provides the user with instructive information through the output means so that the user performs a proper brushing action.

7. The electric toothbrush according to claim 1, wherein
   an output means is provided to output information to the user, and
   the control means determines whether the vibration generation means normally operates according to the output from the acceleration sensor, and when determining the operation of the vibration generation means as abnormal, provides the user with the information on current operation through the output means.

8. The electric toothbrush according to claim 1, wherein one or more selected from a temperature sensor that detects whether the user holds the handle part by hand, an optical sensor that detects a replacement brush is attached to or detached from the toothbrush main body, and a pressure sensor that detects pressure acting on the brush part, are provided, and the control means controls the vibration generation means according to the outputs from these sensors and the output from the acceleration sensor.

* * * * *